(12) United States Patent
Thorpe

(10) Patent No.: US 7,981,135 B2
(45) Date of Patent: Jul. 19, 2011

(54) GARMENT WITH AFFIXED TOURNIQUET

(76) Inventor: Patricia Thorpe, Iowa City, IA (US)

( * ) Notice: Subject to any disclaimer, the term of this patent is extended or adjusted under 35 U.S.C. 154(b) by 130 days.

(21) Appl. No.: 11/955,803

(22) Filed: Dec. 13, 2007

(65) Prior Publication Data

US 2008/0243172 A1    Oct. 2, 2008

Related U.S. Application Data

(63) Continuation-in-part of application No. 11/940,242, filed on Nov. 14, 2007, now abandoned.

(60) Provisional application No. 60/901,715, filed on Feb. 13, 2007, provisional application No. 60/875,087, filed on Dec. 13, 2006.

(51) Int. Cl.
*A61B 17/00* (2006.01)
(52) U.S. Cl. ........................................ 606/203
(58) Field of Classification Search .......... 606/201–204; 24/185, 197, 200
See application file for complete search history.

(56) References Cited

U.S. PATENT DOCUMENTS

| | | | | |
|---|---|---|---|---|
| 2,702,551 | A * | 2/1955 | Hobson | 606/203 |
| 3,969,772 | A * | 7/1976 | Pravaz | 2/79 |
| 4,273,130 | A * | 6/1981 | Simpson | 606/203 |
| 4,770,175 | A * | 9/1988 | McEwen | 606/203 |
| 5,015,251 | A * | 5/1991 | Cherubini | 606/203 |
| 5,604,961 | A * | 2/1997 | Cole | 24/306 |
| 5,695,520 | A * | 12/1997 | Bruckner et al. | 606/204 |
| 5,779,655 | A * | 7/1998 | Holden | 602/5 |
| 6,189,538 | B1 * | 2/2001 | Thorpe | 128/898 |
| 7,604,651 | B1 * | 10/2009 | Harris et al. | 606/203 |
| 2008/0221612 | A1 * | 9/2008 | Rose | 606/203 |

* cited by examiner

*Primary Examiner* — Gary Jackson
*Assistant Examiner* — Christopher Schubert
(74) *Attorney, Agent, or Firm* — Gene Scott; Patent Law & Venture Group

(57) ABSTRACT

The invention provides an article of clothing having a tourniquet affixed to the clothing at one end of the tourniquet, the tourniquet comprising a band comprised of an elastic and flexible material, the band having a width and a length, a first end and a second end, and a first face and second face, where at least a portion of the first face comprises hook-type fastener means, and where the second face comprises loop-type fastener means.

2 Claims, 4 Drawing Sheets

GARMENT WITH AFFIXED TOURNIQUET

PRIORITY

This invention is a continuation-in-part of U.S. patent application Ser. No. 11/940,242, filed Nov. 14, 2007, now abandoned, which is a continuation-in-part of U.S. Provisional Patent Application No. 60/901,715, filed Feb. 13, 2007, and a continuation-in-part of U.S. Provisional Patent Application No. 60/875,087, filed Dec. 13, 2006, the full disclosure of each of which applications are incorporated herein in their entirety.

BACKGROUND OF THE INVENTION

1. Field of the Invention

This invention describes a versatile trauma tourniquet with features permitting ease of application in the field, by incorporation into critical locations on a battle dress uniform or other clothing.

2. Description of Related Art

Wartime trauma from exploding devices and gunshot wounds results in a high incidence of life and limb-threatening injuries. Exsanguination from peripheral vascular injury is the primary preventable cause of death in field trauma, and has been well documented in literature regarding current war trauma.

Blood loss from non-fatal injuries to arms and legs also can contribute to morbidity to kidneys, liver and other vital organs due to hypotension. The loss of significant amounts of blood also increases the rate of consumption of blood products from the blood bank. Multiple extremity wounds can also complicate triage.

It is axiomatic that in combat, there is a "platinum 5 minutes" for major vascular injury. Even with quick triage, it often takes hours to transport casualties off the battlefield, and even if the distance is small, the hazardous nature of the forward combat areas frequently prevents medical personnel from quickly reaching the wounded. Hence the need for individual soldiers to have a readily available tourniquet that is safe and effective.

Thus, despite the advances in modern medical care for the battlefield, control of blood loss is the one immediate treatment that can be applied to or by an injured soldier to decrease the chance of organ injury, limb loss and death due to hemorrhage. A critical immediate danger is always focal vascular injury and uncontrolled hemorrhage.

Despite long-established use in the medical field, the need for new tourniquet technology is readily acknowledged. Hemorrhage from extremity wounds is the leading cause of preventable death on the battlefield, and tourniquets are the most viable option for controlling life-threatening extremity hemorrhage in the tactical phase of an operation. The evolution of tourniquet technology has been a marked response to the realities of fighting in Iraq and Afghanistan.

Tourniquet designs are varied. One recent patent, U.S. Pat. No. 6,189,538, describes a non-pneumatic tourniquet for use in treating deep vein thrombosis that includes a band having a first end and a second end, wherein the first end and second end have a structure for adjustably connecting to one another, shown as hook and loop-type fasteners, and an adjustable disc made of a substantially hard, non-compressible material connected to the band. Provided is a method of treating deep vein thrombosis in which the thrombus cannot be easily treated using a catheter.

U.S. patent application No. 2007/0005107 is directed to a military emergency tourniquet, described as a tourniquet for rapidly and easily reducing or stopping blood flow to a limb. The tourniquet utilizes a hook and loop system and includes a twistable strap, a base including two opposing entry apertures and an exit aperture, a windlass and at least one receiving loop.

U.S. Pat. No. 4,182,338, provides a pressure applying device which prevents bleeding through needle puncture wounds by applying pressure to the wound through an elastomeric appliance having a blunt skin abutting surface held in place over the wound by securing straps. The pressure applied by the device is sufficient only to prevent bleeding through the wound and does not impede the subsurface flow of blood.

The most commonly used tourniquet, however, is still a length of surgical tubing or penrose drain, the tourniquet used in phlebotomy. However, such tubing does not function well for greater than 1-2 minutes because of the pain.

A continuing problem in the field, then, is the need for rapid and safe protection for the soldier for injuries to the extremities. Vascular injury alone can result in amputations from blood loss and resulting ischemic muscle. The existing tourniquets available to the combat infantryman, as well as medical personnel, vary in degree of mechanical/clinical failure, often due to complicated and time consuming application. In addition, certain designs are painful, either inadequately or too adequately diminish blood-flow, or are too bulky for routine field use.

Ease of use and effectiveness of the application are critical to saving lives and limbs during those platinum 5 minutes, yet according to the U.S. Army Institute of Surgical Research, current technology has reportedly fostered misapplications, intolerable pinching and skin/tissue damage, and has yet to take effective control of leg injuries. Studies have shown that tourniquet failure has revolved around several issues: 1) inadequate mechanical advantage for tightening, 2) device failure (i.e., breakage), and 3) intolerable pinching or circumferential pain prior to pulse elimination. While one-handed tourniquet technologies have even been able to minimize blood flow in the arm to some extent, no one-handed technology has been found to be successful in easily and reliably decreasing blood flow to the lower extremity.

In April 2007, a comparative report from The Naval Sea Systems Command was released to the public. This comprehensive review of available field tourniquets compares 13 designs from 12 manufacturers. The comparison was conducted under rigorous clinical standards, and the comments from failed applications provide great insight into the application realities of tourniquet designs. They also demonstrated the need for versatility and immediate availability of a simple, strong and effective tourniquet in the field.

There remains, then, a need for a life and limb saving tourniquet, for military use and other use that can overcome the obstacles of current technology.

SUMMARY OF THE INVENTION

The invention provides an article of clothing, or garment, having a tourniquet affixed to the garment, the tourniquet comprising a band of an elastic and flexible material, the band having a width and a length, a first end and a second end, and a first face and second face, where the first end is attached to the garment and at least a portion of the first face comprises hook-type fastener means, and the second face comprises loop-type fastener means. The tourniquet is lightweight, simple and fast to apply, and effective. In one aspect, the garment can be a battle dress uniform, to make a tourniquet immediately availability to soldiers in battle.

The tourniquet will be affixed to the garment at a region corresponding to any desired region of an appendage, such as the sleeve or pant leg.

In one embodiment, one or more movable discs, secured to the loop side of the tourniquet with hook-type fastener, can be situated to apply focal pressure to a selected location(s) of hemorrhage or sub-surface blood flow.

The garment will be typically provided with sewn-in guide means for holding the tourniquet in encircling position at a desired location around the appendage in its normal, or un-deployed first position. The tourniquet passes through the guide means, which may be a fabric tunnel attached inside the garment, loops, such as belt loops attached inside the garment, or other similar means known for guiding and maintaining encircling material in the garment.

The tourniquet may be affixed such that it encircles an appendage by being extended medially, whereby the first end is pulled post-laterally and secured over the anterior aspect of the appendage. Alternatively, the tourniquet can be affixed such that the tourniquet encircles an appendage by being extended laterally such that the first end is pulled posterio-medially and secured over the anterior aspect of the appendage.

In application, the invention further provides a method for impeding blood flow to an appendage by applying a tourniquet of the garment of the invention, the method comprising extending the first end from the first position to a second position, the second position providing tightening of the tourniquet about the appendage sufficient to control hemorrhage and/or at least partially decrease blood to the appendage, and bringing the hook-type fastener material of the first face into contact with the loop-type fastener means of the second face to secure the tourniquet in the second position.

Through the method, the blood flow may be decreased significantly, by about 50, 60 or 70 percent, or more, as assessed by Doppler flow measurement. The blood flow decrease can also be assessed by distal pulse.

These and other features and advantages of this invention are described in, or are apparent from, the following detailed description of various exemplary embodiments of the apparatus and methods according to this invention.

DETAILED DESCRIPTION OF THE INVENTION

Referring to the above described drawing figures, the present invention provides a versatile tourniquet 2 that can be used in the field by military personnel, by police or emergency personnel, or in a clinical setting by medical personnel, or in civilian applications.

In this description, by the term reversible fastening means is meant any means, such as loop and hook-type fastener material such as Velcro® referred to herein by the terms "loop material" and "hook material," that allows secure fastening of the tourniquet 2, but that can be easily mutually detached or the point of engagement changed to change tourniquet pressure. In the following description the terms "hook material" and "loop material" are frequently used in described embodiments of the present invention, and it will be known by those of skill in the field of this invention, and is meant in this invention, that in all cases, these two materials may be reversed without loss of function or enablement.

By tourniquet 2 is meant any means for impeding blood flow to an appendage or limb by compressing a vessel or series of vessels such as by applying a strap, tube or other means at a region to decrease blood flow to tissue further from the heart. In this description and claims the term "limb" is used and is meant to refer to arms, legs, abdomen neck, head and any other part of the anatomy.

Figure 1:
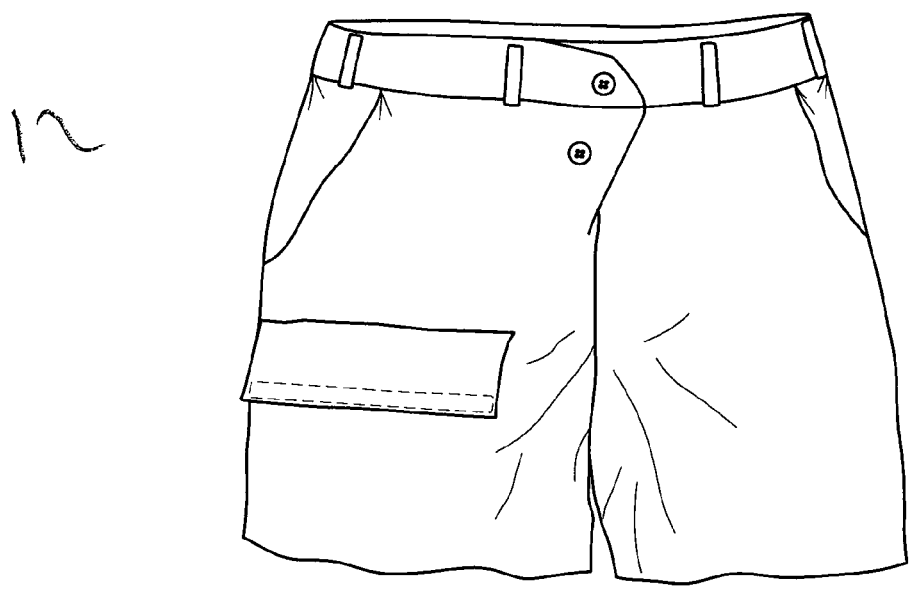
FIG. 1 shows a view of an article of clothing of the invention.

Looking to FIG. 1, there is provided an article of clothing which is referred to herein by the term "garment 1," which can be of any type of fabric and construction. It is contemplated that garment 1 will most commonly be a uniform of police, emergency, security or military personnel. One example is the battle dress uniforms of United States Armed Forces personnel. In FIG. 1, garment 1 is a pair of pants.

Figure 2:
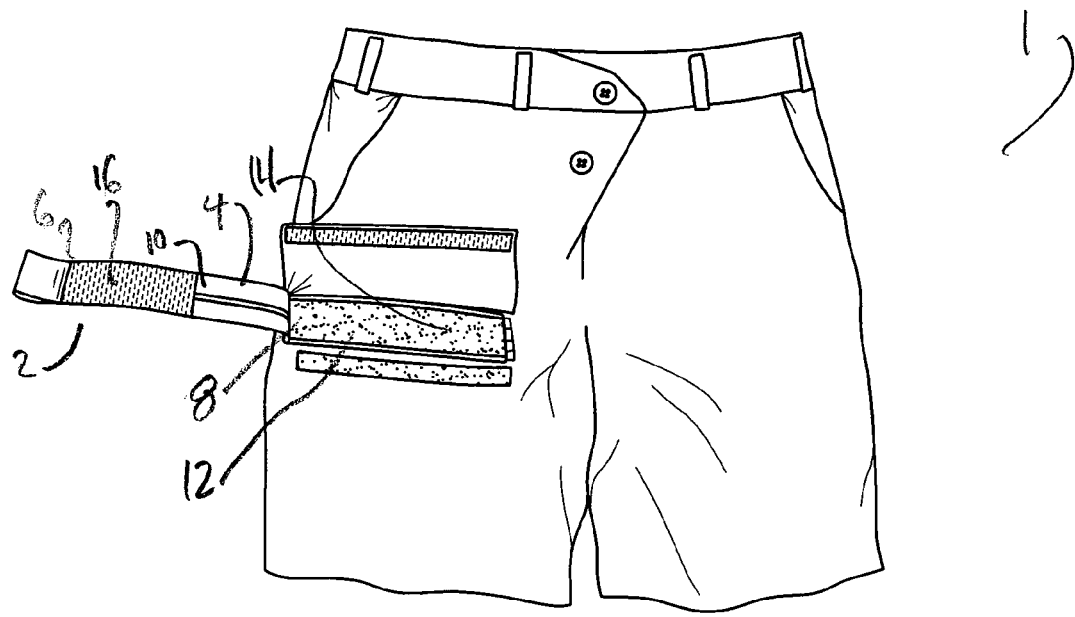
FIG. 2 shows a view of the garment of FIG. 1, with a flap exposed showing the tourniquet.

In reference to FIG. 2, it is seen that tourniquet 2 is affixed to garment 1, although it may not necessarily be fixed but rather just positioned on, and in contact with, the outer surface of garment 1. The tourniquet comprises a band 4 of an elastic and flexible material, the band 4 having a width and a length, a free end 6, and a fixed end 8, attached to the inner surface of garment 1. The tourniquet 2 also has a first face 10 wherein at least a portion of the first face 10 comprises hook material 16.

The width of the band 4 is desirably on the order of about from 1 to 5 inches, or more, the main limitation being that it not be too bulky in forming an integrated part of garment 1. Fabric thickness can vary, depending on the materials, but is on the order of about $1/12$ inch, down to about $1/16$ inch or less, where an appropriate fabric having the strength and elasticity for overall comfort and blood flow restriction is used.

The length of tourniquet 2 may vary. Where the limb is an upper extremity, desirable tourniquet dimensions are from a minimum of about 22 inches up to about 36 inches, or more, as is appropriate for the general population.

For a lower extremity, the minimum dimensions may range between about 30 inches minimum to a maximum of about 42 inches, or more, again, as is appropriate for the general population.

Larger and smaller sizes may be necessitated, depending on the size of the garment 1 and the intended limb. For example, a child's garment 1 would be provided with a shorter tourniquet 2 length.

Figure 3:
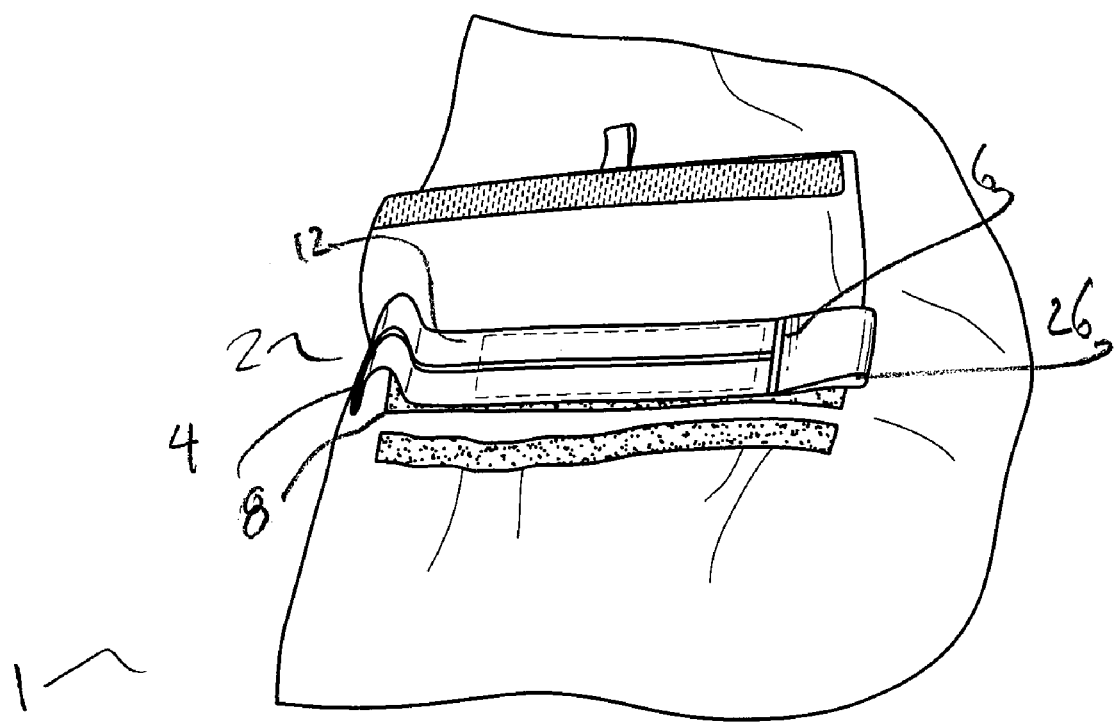
FIG. 3 is an expanded view of the cover-flap of the garment of FIG. 2, demonstrating the presentation of the tourniquet in normal use.

Again in reference to FIGS. 2 and 3, loop material 12 covers the second side of the band between its ends while hook material is mounted first side at the fixed end 8, so as to provide a site for attachment when the tourniquet 2 is moved from its resting attitude to a position for applying tourniquet pressure. The hook material 16 on the first face 10 can vary in length, from a minimum of about 2 inches up to about 9 inches or longer, and can be secured to the band 1 by any means known in the art, such as by being machine stitched, stapled or bonded.

The quality of the reversible fastener system employed should be such that the hook and loop material 16, 12 are able to strongly adhere to each other and also be easily separated when needed.

A pull tab 26 can be supplied at the free end 6 of the tourniquet 2.

Figure 6:
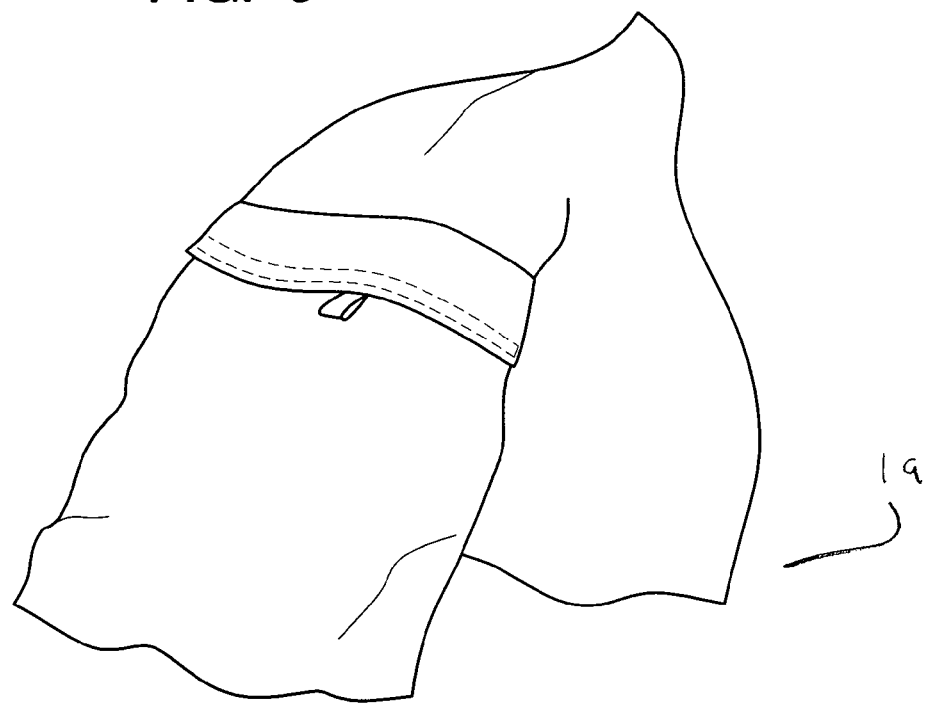
FIG. 6 shows a different garment of the invention.
Figure 7:
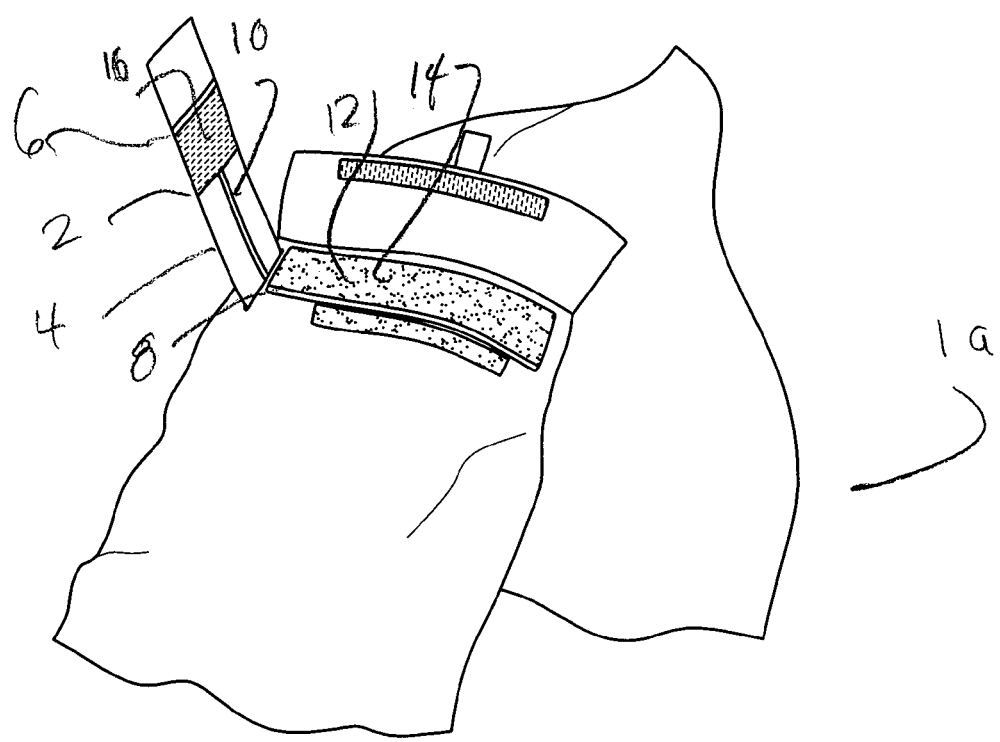
FIG. 7 shows a view of the garment embodiment of FIG. 6, with a flap lifted to expose the tourniquet.

FIGS. 6 and 7 show an alternative embodiment of the invention, where the garment 1 is a shirt rather than pants. The tourniquet 2 is intended to be incorporated directly into the shirt. Tourniquet 2 is light-weight, not bulky and the free end 6 may easily be stored in a provided region in the garment 1 so as to be immediately available for self-deployment including with one-hand activation and release, with essentially no fear of false actuation or failure to deploy or release.

The combining of tourniquet 2 with garment 1 is similar in the shirt version shown in FIGS. 6 and 7, and the pant version of FIGS. 1 through 5, with a similar orientation for the direction of tourniquet 2 with respect to both the garment 1 and the limb, i.e., circumferential. The tourniquet 2 preferably is engaged with the garment 1 so that it encircles the limb, and is pulled at the free end 6, for tightening, toward the centerline of the body.

The advantage of such pull-to-tighten orientation is that either the left or right hand is able to tighten the tourniquet on either left or right arm or leg, in case one arm is injured. Additionally, it enables the use of a person's teeth to grip-and-hold the free end 6 while a free hand moves to a position to adjust the tourniquet or to change gripping positions.

As seen in reference to FIGS. 6 and 7, when engaged with the arm region of garment 1, the orientation of tourniquet 2 is such that the tightened tourniquet 2 will compress the brachial artery just below the axilla, high on the upper arm. The tourniquet 2 is sewn into the garment 1 above the arm pocket between the lapel and the upper arm sleeve seam. It is seen that the arm tourniquet 2 will lift near the front-outside of the arm and stretch while wrapping towards the chest and under the arm and then the free end 6 is attached on the front side to the strip of loop material 12.

In FIG. 2, it is seen that for the pant leg, the orientation of the tourniquet 2 is such primarily circumferential, that when tightened it will compress the femoral artery in the upper thigh. It may be preferable to have a leg tourniquet 2 lift and stretch from the inner thigh aspect and wrap towards the outside of the leg, then around to the back side and through the crotch and attach on the inner front thigh location, in the reverse orientation. Clearly, the tourniquet 2 may be wrapped in either direction around the leg.

Figure 4:
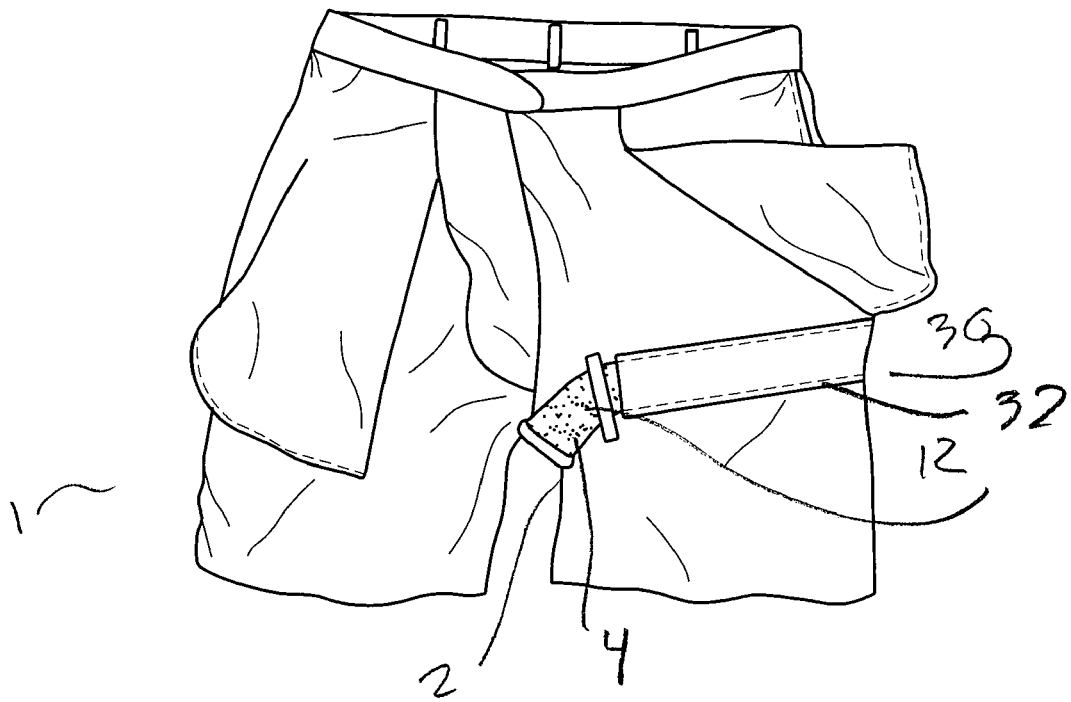
FIG. 4 is an inverted or inside view of an embodiment of the garment showing securement of the tourniquet within the garment.
Figure 5:
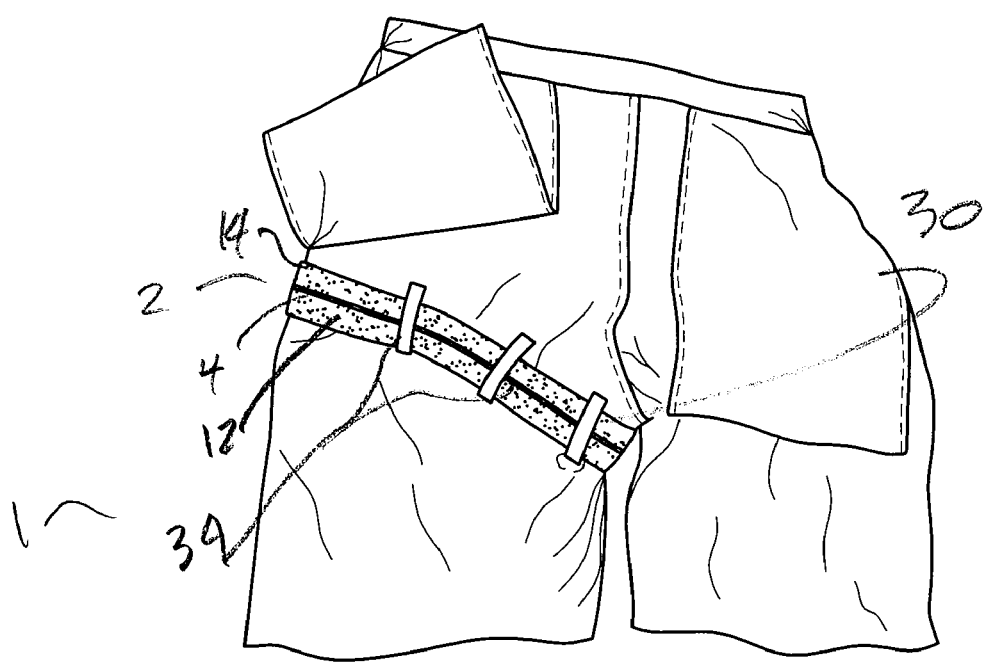
FIG. 5 is an alternate embodiment of the garment, showing a different mechanism of securement of the tourniquet within the garment.

In reference to FIGS. 4 and 5, in the non-tensed state, tourniquet 2 may be held within a sewn-in guide 30 for holding the tourniquet 2 in the desired position around the limb. The tourniquet 2 passes through the guide 30. In FIG. 4 the guide 30 is in the form of a fabric tunnel 32 attached to the inner surface of garment 1, while in FIG. 5 the guide 30 is provided as loops 34, such as belt loops attached to the inner surface of garment 1. Various other means for guiding and maintaining the tourniquet in position are well known to the art.

The band 4 has a width designed to make application of the tourniquet 2 tolerable for a period during which the injured person is transported. The use of a wide elastic band prevents pinching, and the tourniquet 2 can therefore be applied very tightly, when necessary.

Referring to FIG. 2, it is seen that band 4 moves from the non-tensed state to the tensed state by pulling the free end 6 to tighten the tourniquet 2 around the limb, and then securing the tourniquet 2 in the tensed state by placing the hook material 16 of the first face 10 into engagement with the loop material 14 which is fastened to the outer surface of garment 1. The loop material 12 may be a part of the band 4 or may be fixed to band 50, but in either case, the loop material 12 whether part of the band 4 or not is secured to the outside surface of the garment. In the preferred embodiment, the fixed end 8 of band 4 is permanently engaged with the outside surface of the garment 1 and extends through the garment into the interior where it circles the garment 1 as shown in FIGS. 4 and 5 and then immerges through the garment 1 as a free end 6 having hook material 16 ready for being engaged with the loop material 12.

The hook material 16 that is mounted at the free end 6 is used to store the free end 6 in engagement with the loop material 12 when the band 4 is not tensed. The length of the hook material 16 at free end 6 is sufficient to allow the band to engage the loop material 12 when the tourniquet 2 is tensed for applying tourniquet pressure to the limb.

The garment 1 with affixed tourniquet 2 provides a readily available and easily applied mechanism to decrease blood loss immediately after injury. The tourniquet 2 can be applied rapidly to slow blood loss due to vascular injury, and it is possible to apply the tourniquet 2 with one hand, even by an injured patient, because the loop material 12 is fixed in place on garment 1. The tourniquet 2 can be adjusted with one hand, by releasing and changing the position of the hook material 16 on the loop material 12 before engaging again The release is straightforward and quick, but the hook and loop materials 16, 12 provide sufficient strength when engaged to allow prolonged soft tissue compression and control of hemorrhage. The tourniquet 2 can be loosened and re-tightened as necessary.

Rapid control of bleeding without induced ischemia is thus provided by incorporating the tourniquet 2 into the battle dress uniform, for immediate availability to soldiers in battle. When used in this manner the combination of tourniquet 2 and garment 1 could result in decreased mortality, reduced need for transfusion (or the amount thereof), and lower risk of amputation. In the event of trauma to an appendage, tourniquet 2 can typically be applied within 30 seconds to decrease blood loss.

The present invention allows various levels of control of bleeding, and without causing greater injury. The tourniquet 2 is light in weight, packs down to a very small package, and presents no additional risk from heat, such as the risk of flammability as found in rubber tubing tourniquets. Thus, the tourniquet 2 can always be within easy reach and readily and safely deployed.

The tourniquet 2 is also adjustable, in that it is as easy to secure as it is to release, so that quick adjustments can be made, such as for decreasing or increasing the level of tightness, and thus pressure. The ready and simple method of applying the tourniquet 2 permits various levels of pressure, partly due to elasticity of band 4, and as such the blood flow decrease may be partial to substantially complete. The method of use of the present invention can be applied to decrease the distal pulse/blood flow a significant amount, by about 50, 60 or 70 percent, or more, as determined by Doppler flow measurements, though the tourniquet 2 should not, however, be so occlusive that ischemia results from total loss of blood flow.

Individual one-inch, hook and loop-backed, hard foam discs can be strategically inserted under the band 4 by a medic to provide focused pressure over the site or source of blood loss.

While this invention has been described in conjunction with the specific embodiments outlined above, it is evident that many alternatives, modifications and variations will be apparent to those skilled in the art. Accordingly, the preferred embodiments of the invention, as set forth above, are intended to be illustrative, not limiting. Various changes may be made without departing from the spirit and scope of this invention.

I claim:

1. A combination apparatus for applying tourniquet pressure to a limb, the combination apparatus comprising:
    a clothing garment having a tubular portion, the tubular portion providing an outer surface and an inner surface;
    a tourniquet comprising an elongated elastic band with a fixed end of the band positioned on the outer surface of the garment and directly secured thereto when a flap extending over the fixed end of the band is raised, the band extending from the fixed end, in proximity to the inner surface of the garment, circularly around the tubular portion, and terminating at a free end extending in proximity to the fixed end at the outer surface of the garment;
    a loop material covering the band and facing the limb, and a hook material covering the fixed end of the band and facing away from the outer surface of the garment;
    wherein the band may be tightened or loosened around the limb by elastically extending the band and selectively positioning and engaging the loop material engaged with the hooked material to thereby secure the band in place around the limb with a selected tension.

2. A method of applying tourniquet pressure to a limb, the method comprising the steps of:
    providing a clothing garment having a tubular portion, the tubular portion providing an outer surface and an inner surface;
    providing a tourniquet comprising an elongated elastic band with a fixed end of the band positioned on the outer surface of the garment and directly secured thereto when a flap extending over the fixed end of the band is raised, the band extending from the fixed end, in proximity to the inner surface of the garment, circularly around the tubular portion, and terminating at a free end extending in proximity to the fixed end at the outer surface of the garment;
    providing a loop material covering the band and facing the limb, and a hook material covering the fixed end of the band and facing away from the outer surface of the garment;
    engaging the fixed end of the elastic tourniquet band with the outer surface of the tubular portion of the clothing garment when the flap of the garment is raised;
    extending the band circularly in proximity to an inner surface of the garment;
    extending a free end of the band through the garment into proximity with the fixed end of the band;
    fixing hook material on the fixed end of the tourniquet band with loop material on the free end of the tourniquet band thereby establishing pressure on the limb.

* * * * *